(12) United States Patent
Mahon et al.

(10) Patent No.: US 9,770,607 B2
(45) Date of Patent: *Sep. 26, 2017

(54) FLUID CIRCUITS FOR TEMPERATURE CONTROL IN A THERMAL THERAPY SYSTEM

(71) Applicant: Profound Medical Inc., Mississauga (CA)

(72) Inventors: Cameron Mahon, Georgetown (CA); Sean Donaldson, Toronto (CA)

(73) Assignee: Profound Medical Inc., Mississauga, ON (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/267,800

(22) Filed: Sep. 16, 2016

(65) Prior Publication Data

US 2017/0001044 A1    Jan. 5, 2017

Related U.S. Application Data

(63) Continuation of application No. 12/932,914, filed on Mar. 9, 2011, now Pat. No. 9,566,455.

(Continued)

(51) Int. Cl.
*A61N 7/02* (2006.01)
*A61B 17/00* (2006.01)
(Continued)

(52) U.S. Cl.
CPC .... *A61N 7/022* (2013.01); *A61B 2017/00084* (2013.01); *A61B 2017/00092* (2013.01);
(Continued)

(58) Field of Classification Search
CPC .......... A61N 7/022; A61B 2017/00084; A61B 2017/00092; A61B 2090/374; A61B 2017/00023
See application file for complete search history.

(56) References Cited

U.S. PATENT DOCUMENTS 3,757,356 A    9/1973  Freeman
4,791,930 A   12/1988  Suzuki et al.
(Continued)

OTHER PUBLICATIONS

US ISA, "International Search Report—App. No. PCT/US11/00441", May 6, 2011, WIPO.

*Primary Examiner* — Katherine Fernandez
*Assistant Examiner* — Colin T Sakamoto
(74) *Attorney, Agent, or Firm* — Intrinsic Law Corp.

(57) ABSTRACT

A system and method for fluid control in a thermal therapy system is disclosed. A fluid circuit permits passage of a fluid through a fluid circuit, including into and out of a treatment zone so as to cool or heat or maintain a temperature in said treatment zone at or near a desired temperature. The temperature is sensed at a point in the circuit between a discharge of a fluid pump and the treatment zone. MRI based thermometry of tissue in the treatment zone is accomplished in some aspects. Furthermore, a desired temperature may be programmably set to a given value or within a band of values using a processor and a temperature controller. In some aspects, leakage of fluid from a patient or from the fluid control system is captured by a leak-proof member to protect imaging and treatment equipment from damage.

20 Claims, 4 Drawing Sheets

Related U.S. Application Data (60) Provisional application No. 61/311,837, filed on Mar. 9, 2010.

(51) Int. Cl.
  *A61B 18/00* (2006.01)
  *A61B 90/00* (2016.01)

(52) U.S. Cl.
  CPC .............. *A61B 2018/00023* (2013.01); *A61B 2090/374* (2016.02)

(56) References Cited

U.S. PATENT DOCUMENTS

| | | | |
|---|---|---|---|
| 5,295,484 A | 3/1994 | Marcus et al. | |
| 5,500,267 A | 3/1996 | Canning | |
| 5,593,415 A | 1/1997 | Adrian | |
| 5,601,526 A | 2/1997 | Chapelon et al. | |
| 5,620,479 A | 4/1997 | Diederich | |
| 5,647,361 A | 7/1997 | Damadian | |
| 5,733,315 A | 3/1998 | Burdette et al. | |
| 6,050,943 A | 4/2000 | Slayton et al. | |
| 6,077,257 A | 6/2000 | Edwards et al. | |
| 6,122,551 A | 9/2000 | Rudie et al. | |
| 6,379,320 B1 | 4/2002 | Lafon et al. | |
| 6,393,314 B1 | 5/2002 | Watkins et al. | |
| 6,418,337 B1 | 7/2002 | Torchia et al. | |
| 6,432,067 B1 | 8/2002 | Martin et al. | |
| 6,490,488 B1 | 12/2002 | Rudie et al. | |
| 6,500,121 B1 | 12/2002 | Slayton et al. | |
| 6,516,211 B1 | 2/2003 | Acker et al. | |
| 6,522,142 B1 | 2/2003 | Freundlich | |
| 6,537,306 B1 | 3/2003 | Burdette et al. | |
| 6,542,767 B1 | 4/2003 | McNichols et al. | |
| 6,559,644 B2 | 5/2003 | Freundlich et al. | |
| 6,582,381 B1 | 6/2003 | Yehezkeli et al. | |
| 6,589,174 B1 | 7/2003 | Chopra et al. | |
| 6,618,608 B1 | 9/2003 | Watkins et al. | |
| 6,618,620 B1 | 9/2003 | Freundlich et al. | |
| 6,623,430 B1 | 9/2003 | Slayton et al. | |
| 6,637,538 B2 * | 10/2003 | Morykon | F16B 21/18 180/313 |
| 6,671,535 B1 | 12/2003 | McNichols et al. | |
| 6,692,450 B1 | 2/2004 | Coleman | |
| 6,692,518 B2 | 2/2004 | Carson | |
| 6,735,461 B2 | 5/2004 | Vitek et al. | |
| 6,746,465 B2 | 6/2004 | Diederich et al. | |
| 6,755,849 B1 | 6/2004 | Gowda et al. | |
| 6,818,012 B2 | 11/2004 | Ellingboe | |
| 7,069,976 B2 | 7/2006 | Lindgren | |
| 7,135,029 B2 | 11/2006 | Makin et al. | |
| 7,167,741 B2 | 1/2007 | Torchia et al. | |
| 7,229,411 B2 | 6/2007 | Slayton et al. | |
| 7,344,529 B2 | 3/2008 | Torchia et al. | |
| 7,473,224 B2 | 1/2009 | Makin | |
| 7,771,418 B2 | 8/2010 | Chopra et al. | |
| 7,806,892 B2 | 10/2010 | Makin et al. | |
| 7,951,182 B2 | 5/2011 | Stelea et al. | |
| 7,993,289 B2 | 8/2011 | Quistgaard et al. | |
| 8,021,406 B2 | 9/2011 | Cazzini et al. | |
| 8,025,688 B2 | 9/2011 | Diederich et al. | |
| 2003/0018266 A1 | 1/2003 | Makin et al. | |
| 2003/0069502 A1 | 4/2003 | Makin et al. | |
| 2003/0092988 A1 | 5/2003 | Makin | |
| 2006/0173344 A1 * | 8/2006 | Marian | A61B 8/00 600/459 |
| 2006/0241442 A1 | 10/2006 | Barthe et al. | |
| 2007/0239062 A1 | 10/2007 | Chopra et al. | |
| 2008/0015505 A1 * | 1/2008 | Trombley | A61M 5/142 604/151 |
| 2008/0058697 A1 | 3/2008 | Kamen et al. | |
| 2008/0242970 A1 | 10/2008 | Minagawa et al. | |
| 2009/0143775 A1 | 6/2009 | Rizoiu et al. | |
| 2009/0171185 A1 | 7/2009 | Chou et al. | |
| 2009/0259121 A1 * | 10/2009 | Simonetti | A61B 5/0046 600/410 |
| 2011/0203788 A1 | 8/2011 | Kato | |
| 2011/0259121 A1 * | 10/2011 | Kolahi | G01F 1/8409 73/861.355 |
| 2011/0301508 A1 | 12/2011 | Sethuraman et al. | |

* cited by examiner

FLUID CIRCUITS FOR TEMPERATURE CONTROL IN A THERMAL THERAPY SYSTEM

CROSS-REFERENCE TO RELATED APPLICATIONS

The present application claims priority to U.S. patent application Ser. No. 12/932,914, bearing the present title, filed on Mar. 9, 2011, which claims priority to U.S. Provisional Application No. 61/311,837, bearing the present title, filed on Mar. 9, 2010, which are hereby incorporated by reference.

TECHNICAL FIELD

The present application relates to ultrasound therapy systems, and particularly to ways for controlling a temperature (e.g., cooling) of a thermal therapy applicator and/or the regions of tissue proximal to the same within a patient undergoing thermal therapy such as ultrasound thermal therapy.

BACKGROUND

Ultrasonic transducers have been employed in ultrasound therapy systems to achieve therapeutic heating of diseased and other tissues. Arrays of ultrasound transducers operating to form a beam of ultrasonic energy cause a conversion of sound to thermal energy in the affected tissue areas or treatment volumes, and a subsequent beneficial rise in the temperature in the treatment volumes. With proper monitoring of the heating effect, ultrasound therapy systems can be used to treat harmful cells and to controllably destroy cancerous tumors.

As known to those skilled in the art, ultrasonic transducers are constructed and operated to take electrical power and produce ultrasound energy waves from a surface of a transducer element in a process generally referred to as transduction. The nature and extent of the transduction depends on the material used to construct the transducers, transducer geometry, and the electrical input to the transducers. A common material used in construction of ultrasound transducers is piezo-electric transducer crystal material, e.g., lead zirconate titanate (PZT).

One challenge in constructing clinically-usable systems for image-guided therapy is in constructing the electrical, mechanical, and electro-mechanical support systems for providing thermal therapy to a patient. This is especially true if part of the system needs to reside in an environment having strong magnetic fields such as is found in magnetic resonance imaging (MRI) environments.

It is useful to have a controllable and sterile system for controlling a temperature of a therapy device in a patient during a thermal therapy treatment procedure.

SUMMARY

Embodiments hereof are directed to systems and methods for providing a thermal therapy applicator and supporting components that is suitable for ultrasonic thermal therapy treatments in an image-guided environment such as in magnetic resonance imaging (MRI) environments.

Aspects of the present disclosure provide fluid handling loops suitable for operation during image-guided thermal therapy and clinically sterile for penetration into patients and patient treatment applicators.

One embodiment is directed to a fluid control system for use in a thermal therapy system, the fluid control system comprising a volume for filling with a fluid, said fluid adapted for flow through a fluid circuit portion of said apparatus; a pressure source that drives said fluid through said fluid circuit; an inlet portion of said fluid circuit that allows said fluid to pass into a portion of said thermal therapy system; an outlet portion of said fluid circuit that allows said fluid to pass out of said portion of said thermal therapy system; a temperature sensor that senses a temperature of said fluid, or a temperature of a patient's tissue proximal to a position of said temperature sensor, and provides a corresponding temperature sensor output signal indicative of said temperature; a temperature controller that receives said temperature sensor output signal and that receives a reference signal indicative of a desired temperature setting, and that provides an output control signal; and a thermal element that receives said output control signal and that acts to change the quantity of heat energy in the fluid so as to maintain the temperature of said fluid substantially at or near the desired temperature setting. Another embodiment is directed to a method for controlling a fluid in a thermal therapy system, comprising providing a fluid in a fluid circuit; pumping said fluid through an inlet portion of the fluid circuit to a location proximal to which a temperature is to be controlled; receiving a return of said fluid from said location into a return portion of said fluid circuit; measuring a temperature of said fluid substantially at or proximal to said location and generating a temperature sensing signal corresponding to said temperature; comparing said temperature sensing signal to a reference signal; and controlling a heat element to add heat to said fluid if its temperature drops below a desired setting or to remove temperature from said fluid if its temperature rises above said desired setting.

BRIEF DESCRIPTION OF THE DRAWINGS

For a fuller understanding of the nature and advantages of the present invention, reference is be made to the following detailed description of preferred embodiments and in connection with the accompanying drawings, in which.

DETAILED DESCRIPTION

As discussed above, better understanding of the electrical response of ultrasound transducers in therapeutic systems is useful for improving the effectiveness of such systems and delivering safe efficient treatment to patients.

Figure 1:
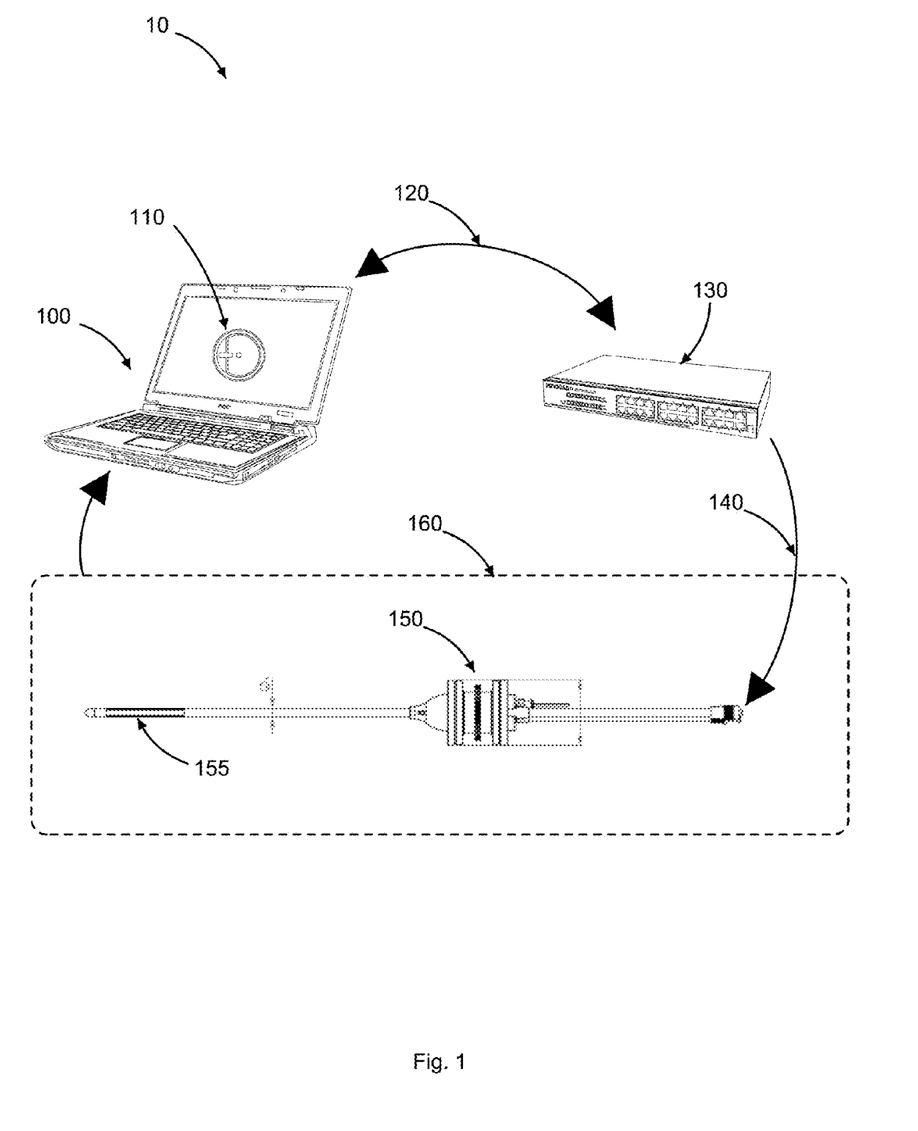
FIG. 1 illustrates an exemplary system for providing image-guided ultrasound therapy to a patient.

FIG. 1 illustrates an exemplary system 10 for providing image-guided ultrasound therapy to a patient. The simplified illustration shows a master computer 100, such as a portable PC, workstation, or other processing device having a processor, memory, and coupled to some input/output apparatus. Master computer 100 may include a display and may support a user interface 110 to facilitate control of and observation of the thermal therapy treatment process.

Master computer 100 is adapted for coupling to other systems and components through a computer interface connector 120. Connection 120 carries data and information to and from master computer 100 and may comprise standard or special-purpose electrical wiring connection cables, such as serial connection cables or the like. Also, connection 120 may be achieved wirelessly as known to those skilled in the art of wireless communication, and may further be achieved by way of multiple connections, over a network, or by another suitable method.

In some embodiments, master computer 100 is coupled through connection 120 to a power control unit 130. Power control unit 130 may be implemented as a stand-alone hardware apparatus but may be implemented as a part of master computer 100, e.g., by being built onto a special card in a computer or server system that accommodates such hardware components.

Power control unit 130 may specifically include at least a processor adapted for processing machine or program instructions, which may be provided to the processor from another component of system 10 and may be stored on a memory device in power control unit 130. Circuitry including analog and/or digital circuitry may be operated within power control unit 130 so as to determine an output power to one or more ultrasound therapy transducer elements in an ultrasound therapy apparatus 150.

In some embodiments, power control unit 130 may deliver controlled electrical driving signals to a plurality of ultrasound transducer elements (e.g., PZT array elements) in ultrasound therapy apparatus 150. The driving signals may be controlled to deliver a programmed amount of power to each element or to groups of elements of therapy apparatus 150. The driving signals may also be controlled so as to provide a determined driving voltage, current, amplitude, waveform, or frequency to said ultrasonic transducers of therapy apparatus 150. Such electrical driving signals are carried from power control unit 130 to the ultrasound therapy apparatus 150 over suitable wires, cables, or buses 140. Appropriate plug interfaces or connectors may be included so as to mate the various ends of the connectors or buses to and from their associated components.

In operation, ultrasound therapy apparatus 150 includes a portion 155 that is inserted into a portion of a patient's body to deliver a suitable dose of ultrasound energy to tissue in a diseased region of the patient's body.

The patient and the ultrasound therapy apparatus 150 are generally disposed in an imaging volume 160 such as a magnetic resonance imaging (MRI) apparatus, which can provide real-time images of the relevant parts of the patient, e.g., the treatment volume to master computer 100 or display and user interface 110. In some embodiments, real-time monitoring of the thermal therapy is performed so that a clinical operator can monitor the progress of the therapy within the treatment volume or diseased tissue. Manual or automated changes can be made to the power signals from power control unit 130 based on input from the results and progress of the treatment.

The feedback and coupling of the treatment system components to the control components in system 10 can be used to ensure that an optimum radio frequency (RF) power signal is provided to each element of an ultrasound array 155 used in treatment of diseased tissues. Some examples include treatment of prostate cancer tumors in male patients using MRI guided ultrasound therapy applications.

RF power control unit 130 may include separate circuit cards having individual processors, amplifiers, filters and other components to achieve the desired driving power output to the elements of ultrasound array 155 of ultrasound treatment apparatus 150. Alternatively, a single processor may be employed to control the behavior of the various power channels to each array element.

In the embodiments described below, a fluid system is used to control the temperature of the thermal therapy apparatus or applicator and/or to control a temperature of a region of tissue proximal to the therapy applicator.

Figure 2:
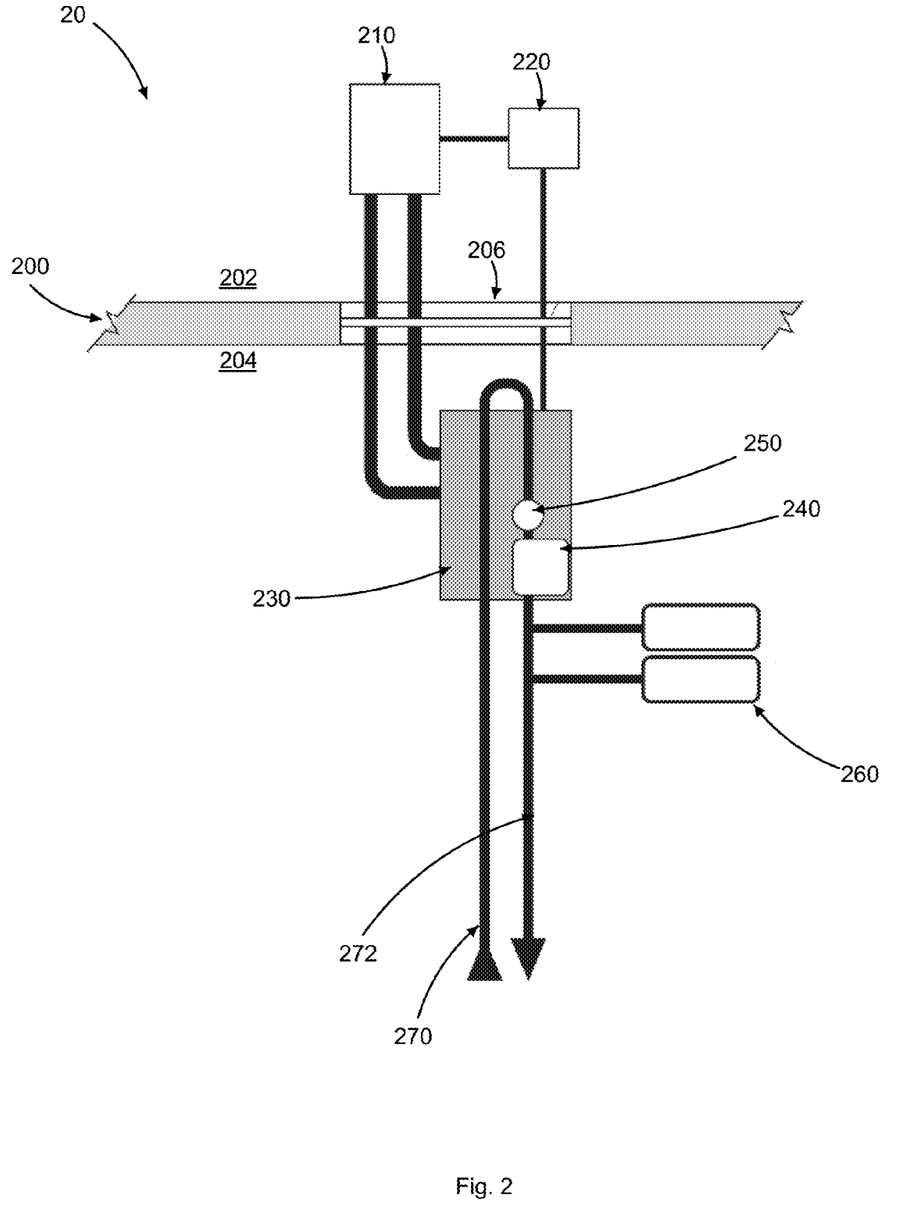
FIG. 2 illustrates an exemplary fluid processing system including a primary and a secondary fluid circuit for controlling a temperature in and/or around a thermal therapy applicator.

FIG. 2 illustrates a system 20 for providing and controlling fluid delivery to and from a thermal therapy applicator. The fluid may be used to cool (or heat) various components of the thermal therapy applicator. The fluid may also cause the tissues adjacent to the applicator apparatus to be affected so as to prevent unwanted overheating of a region of healthy tissue directly proximal to an ultrasound applicator.

As is known to those skilled in the art, magnetic imaging environments such as MRI environments are subjected to strong magnetic fields from one or more magnets used in the MRI imager apparatus. For this reason, it is often difficult to have equipment within a MRI environment that is affected by such strong magnetic fields. Therefore, pumps, motors, heaters, electronic systems, computers, and other electromechanical apparatus are affected or even damaged by magnetic fields used in MRI environments.

Accordingly, MRI centers usually employ magnetic shielding walls, sometimes Faraday chambers or conductive sheathing, to shield the interior of the MRI environment from the operational environment outside the MRI environment.

In FIG. 2 such a shielding wall 200 is shown that defines a magnetized environment 204 within the magnetic (MRI) imaging chamber and a non-magnetized environment 202 that is outside, or shielded from, the magnetic environment. Computers and other electro-mechanical devices can be used in the non-magnetized environment 202 because wall 200 shields environment 202 from the heavy magnetic fields and associated induction currents present inside magnetized imaging environment 204. Inside the magnetized chamber 204, equipment should preferably be immune to magnetic fields and induction currents. Equipment made of non-ferrous or non-magnetizable components is usually able to operate normally within magnetic environments. Ceramic and plastic materials are examples of materials that can be used to construct mechanical components for use in such magnetic environments.

In operating systems requiring some components to be within the magnetized space 204 and others to be in non-magnetized space 202, a penetration panel 206 is provided to allow passage of electrical cabling and/or fluid tubing between the sides 204 and 202 of wall 200.

As is also known to those skilled in the art, magnetic imaging environments such as MRI environments may be disturbed by the presence of electrical interference at or near the Larmor frequency. For this reason, it is sometimes difficult to have electrical equipment within a MRI environment because it may adversely affect the detection of small magnetic fields that are used to generate the MR image. Therefore, pumps, motors, heaters, electronic systems, computers, and other electro-mechanical apparatus can prevent the MRI from functioning as intended or may detract from the quality of its operation.

Upon examination of the fluid system of FIG. 2, it is apparent that two distinct fluid loops are used to provide the instant temperature control. First, a "primary" fluid loop drawn near the bottom of FIG. 2 is used to deliver fluid in a first fluid circuit into and then out of a patient's body by way of the thermal therapy applicator apparatus as described in other applications by the present inventors and assignee. This primary fluid circuit controls the temperature of the apparatus and the patient's tissue near the apparatus and the primary fluid circuit resides in components shown within the magnetized imaging and treatment environment 204. Another fluid circuit, which may be denoted as a "secondary" fluid loop is used to control the temperature of the first "primary" fluid loop. In general, the fluid systems are used for cooling, or removal of heat energy from the therapy device and the patient, but the present discussion is not so limiting. The secondary fluid circuit extends into the upper non-magnetized space 202, where it can be cooled by external means.

In operation, the primary fluid loop delivers cooling (or generally temperature-control) fluid to the patient by way of the therapy apparatus through piping line or duct or tube 272. The return path of the primary fluid is through piping or ducting or tubing 270. Generally, in a cooling scenario, the temperature of the fluid entering the patient through line 272 is lower than the temperature of the fluid leaving the patient through line 270. The amount of thermal energy being removed per unit time can be easily computed by knowing the difference in temperature between the fluid in lines 272 and 270 and knowing the volumetric flow rate of the fluid therein. Because cooling fluids (e.g., water, saline) are essentially incompressible, a fluid flow measuring device can be installed in one or both legs 272, 270 to measure and report the primary fluid loop volumetric flow rate. Similarly, thermometric devices in legs 270 and 272 can be used to record and report the temperature in the ingress and egress legs of the primary fluid circuit.

The primary fluid circuit is preferably kept short and near the treatment device and patient within chamber 204. This minimizes the frictional "head loss" in the circuit and reduces the distance over which the primary cooling fluid needs to be transported during operation. In one respect, this simplifies the design and lowers the cost of the system.

A Sterile fluid pump 240 such as a peristaltic pump may be used to move primary cooling fluid through the primary fluid circuit. Thermal sensor 250 records the measured temperature of the fluid and can provide an input to a fluid pump controller circuit. A fluid fill and gas removal apparatus 260 is coupled to the primary fluid circuit to remove gas (e.g., air) bubbles from the circuit and to fill and maintain the circuit. It is understood that other components such as sensors and filters may also be included in the primary fluid circuit.

The heat collected by the fluid in the primary fluid circuit is cooled in a thermal transfer block heat exchanger 230, where the secondary fluid removes the heat from the primary fluid without coming into contact with it. Convoluted tubing or heat exchanger fins within thermal transfer block 230 may be used to enhance the heat exchange characteristics of block 230. The temperature control system can apply a temperature modulation to set the temperature of the circulating fluid to a given setting or within a given temperature band (min, max) as desired. In some embodiments, the temperature is monitored at one or more locations in the fluid circuit, e.g. at a given location proximal to key patient organs, and the temperature modulation is designed to protect such key organs from damage due to unwanted exposure to heating or cooling during operation of the system.

Secondary fluid is moved using a fluid heater and pumping unit 210, which is controlled by a temperature control unit 220. The temperature control provides heating and/or cooling of the circulating fluid, for example, heating the fluid if its temperature drops below a given temperature due to heat loss to the environment where the fluid is stored and circulated, or, cooling the fluid if its temperature exceeds a given set point from exposure to ultrasound energy, heated tissue, electrical components, etc.

The pumping unit of 210 may include any known useful pumps, including magnetically driven motorized pumps, peristaltic pumps, displacement or reciprocating pumps and the like. The temperature control unit 220 provides a signal to control the pumping of the secondary fluid within the secondary fluid loop, and in turn through thermal transfer block 230. Again, calculation of the rate of thermal energy removal (or addition) in the system overall can be computed by placement of temperature sensors in the secondary flow loop and knowledge of the volumetric flow rate therein.

The penetration panel 206 may include custom or standard fittings for passage of the secondary fluid across the wall 200. The secondary fluid does not necessarily have to be sterile, and can be substantially longer (not shown to scale in the drawing) than the length of the primary fluid tubing. Continuous tubing may be passed through wall 200 to move the secondary cooling fluid through wall penetrations in penetration panel 206. Alternatively, separate tubing may be provided in the secondary fluid loop for sides 202 and 204 so that fittings are used to connect the inner (on side 204) and outer (on side 202) portions of the secondary fluid loop as is described in related applications to the present assignee.

Either the primary or the secondary fluid flow loops may be used to control the cooling or heating to the thermal therapy device and patient, or a combination of both the primary and secondary loops may be controlled together to achieve the optimal thermal energy movement to or from the therapy device and patient.

Figure 3:
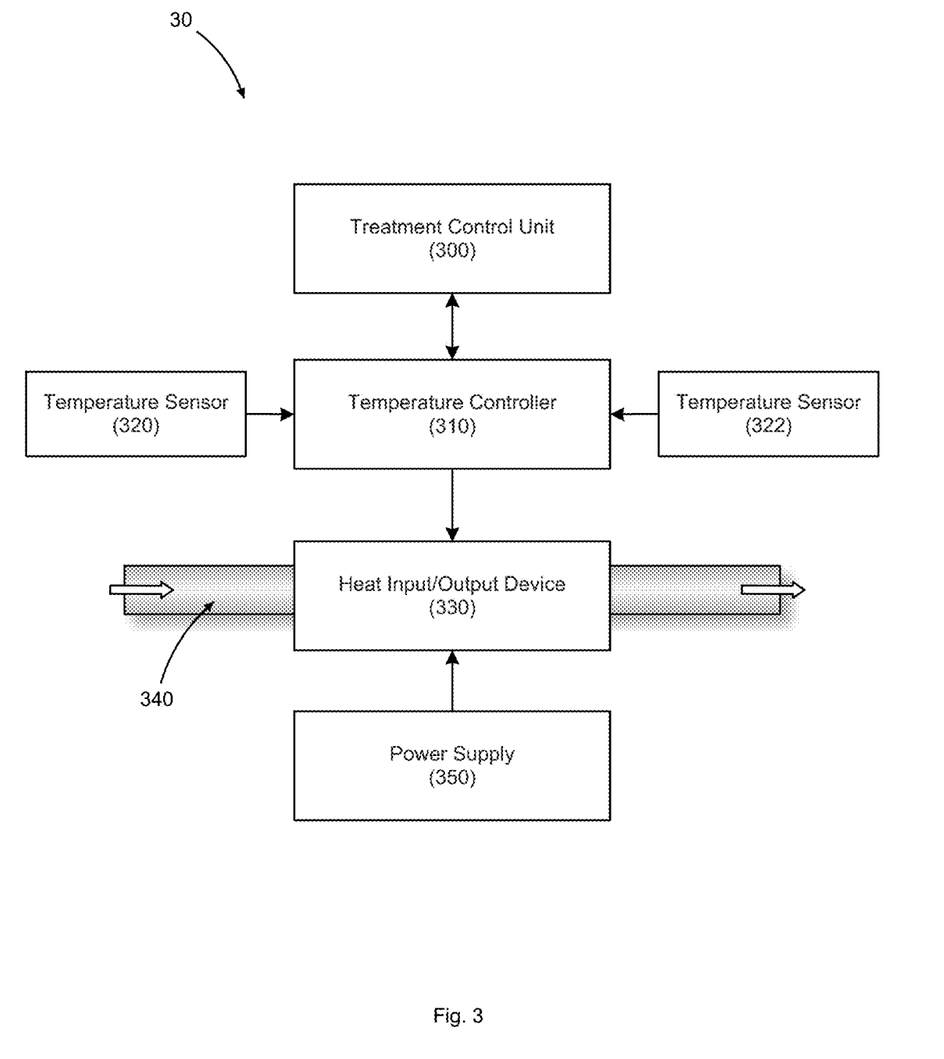
FIG. 3 illustrates a schematic exemplary temperature control system.

FIG. 3 illustrates an exemplary sterile fluid loop temperature control system 30. A temperature control unit 300 includes circuitry and instructions for accepting inputs and providing outputs including for temperature control of the afore mentioned fluid circuit. A processor or computer CPU can process information as required and interfaces to other components such as a temperature controller 310. Note that the temperature controller 310 may be implemented as a single apparatus along with the treatment control unit or as a separate circuit or component as desired in a given application using separate or combined hardware and software to accomplish the purpose of the system.

In some embodiments, the treatment control unit 300 acts on stored or input data to determine a temperature setting desired at one or more locations within the fluid loop. In one example, the temperature sensor 320 is located proximal to a sensitive patient organ, e.g. neuro-vascular bundles, or other healthy tissues that are not to be over-heated or over-cooled.

In another embodiment, a temperature sensor e.g. 322 is located at a key location in the fluid circuit, for example at a discharge of a pump or in a fluid storage reservoir. The pump acts as a pressure source to drive the movement of the fluid through the system's fluid circuit. The treatment control unit 300 sends temperature control signals to temperature controller 310 so that temperature controller 310 can act to control a heat input/output device 330 to maintain the temperature in the fluid circuit or locations therein.

Temperature controller 310 is coupled to exchange signals with treatment control unit 300 as described above. Temperature controller 310 also receives input signals from one or more temperature sensors, e.g., IR sensors, bimetallic sensors, thermocouples or other sensors, to measure the temperature of the fluid at corresponding one or more locations. Temperature controller 310 also sends control signals to activate or control the heat input/output device 330. The heat input/output device 330 is meant to anticipate a heater element, heating coil, radiative heater, or other means of adding heat to the fluid; or a cooler, chiller, or other means of removing heat from the fluid. Therefore, for the present purposes, we can refer to heat input/output device 330 generally (regardless of whether it is used for heating or cooling the fluid) because it causes the addition of heat, removal of heat, or both the addition and removal of heat from the fluid. So in some embodiments separate heating and cooling elements are used, whereas in other embodiments a single heat pump or other means can achieve both heating and cooling as needed. In yet other embodiments a heater and a chiller are both used in series and one or both are controlled by the temperature controller 310 as needed.

As said before, temperature controller 310 can act to keep fluid 340 at a set temperature as indicated by temperature control unit 300 in some embodiments. In other embodiments, a preset or programmed band of temperatures sets a minimum and a maximum temperature range within which fluid 340 is to be maintained. A pair of limit switches coupled to corresponding sensors can be used to activate a heating or cooling cycle. The settings and ranges of temperatures desired can be based on avoiding unwanted thermal damage to areas of the patient such as his reproductive, nervous, circulatory, or waste removal organs. In some specific embodiments, the temperature setting or temperature band is set to maintain the fluid and/or the patient's tissue at a temperature substantially similar to the body's normal internal temperature.

It can be appreciated by those skilled in the art that the present temperature control system 30 might also be used to promote certain therapeutic effects. For example, if the location and nature of the patient's disease is such that the therapy can benefit from local heating of the tissue in the treatment zone using the circulating fluid then this can be accomplished. For example, the fluid in one part of the fluid circuit may be heated to a given temperature before or during the therapy. However, this is not required in many preferred embodiments.

For the sake of further clarity, we describe next a preferred embodiment hereof. A patient having prostate cancer is presented for treatment. The entire prostate, or diseased portions thereof, are to be treated using a thermal therapy procedure. Treatment by hyperthermia from an array of ultrasound transducers electrically driven and electronically is a preferred embodiment. The ultrasound therapy applicator may be inserted into the patient's urethra and up to a place within the treatment zone in the prostate, which surrounds the urethra. The ultrasonic elements of the array are driven in magnitude and waveform so as to cause deposition of ultrasound energy into the diseased tissue. The diseased tissue is thus heated and upon reaching a certain temperature and/or thermal dose the cells of the diseased tissue (e.g., cancer cells) are destroyed. Fluid is circulated in the treatment apparatus as described above, said circulation of fluid moving in and out of the treatment zone proximal to an in the patient's body, and on to the rest of the circuit, which is preferably kept sterile and at a known temperature or in a given range of temperatures at key locations in the circuit. In one specific preferred embodiment, the temperature of the circulating fluid is monitored just downstream of (near the discharge of) the pressure driver (pump). The temperature of the circulating fluid is maintained and monitored thus by using a temperature sensor (e.g., infrared "IR" sensor) coupled to a temperature controller circuit. The temperature controller circuit causes a thermal element (heater in one embodiment) to heat the fluid. In an aspect, the fluid may be heated by the thermal element/heater and may cool by heat loss to the environment and other components of the system. However, this is not limiting, and the fluid thermal element may cool the fluid as well if needed.

Figure 4:
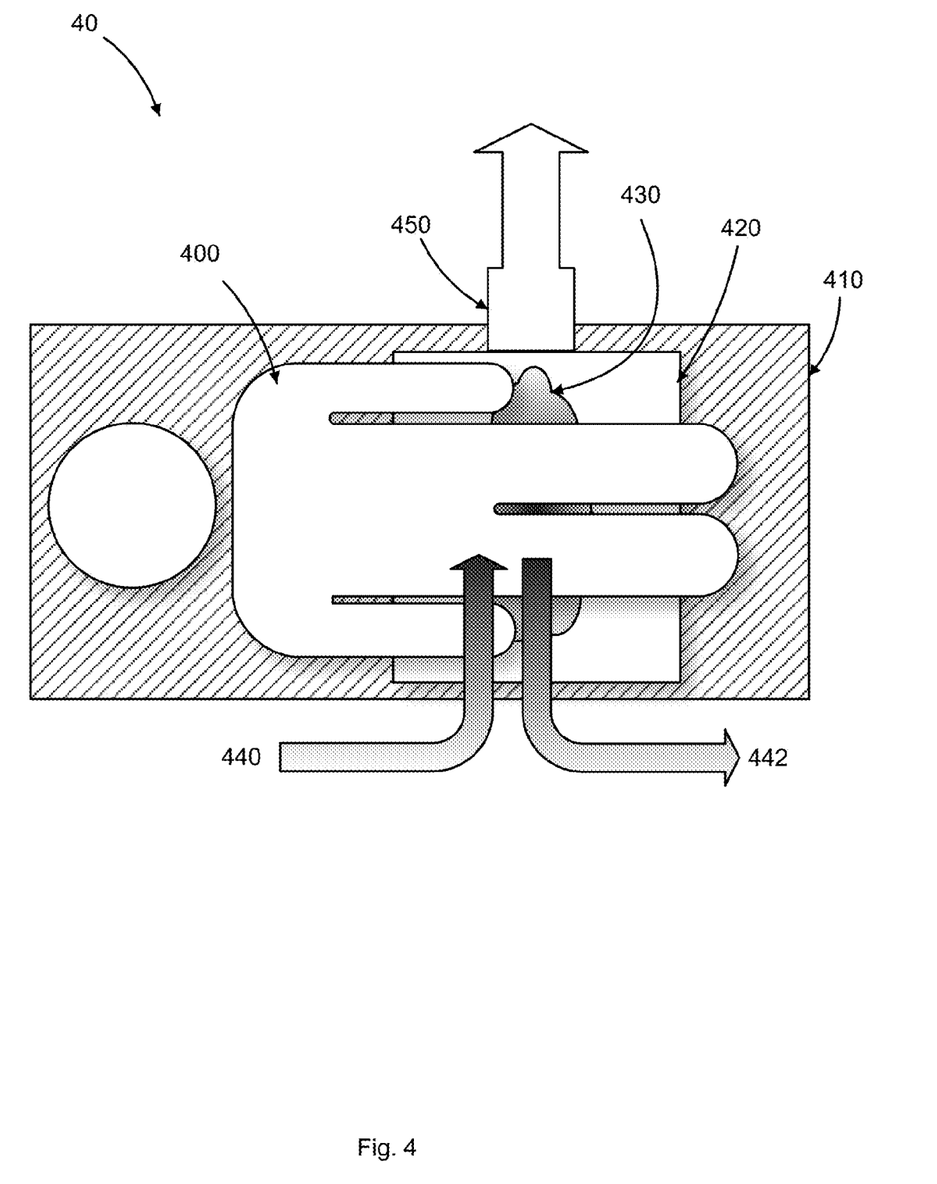
FIG. 4 illustrates a simplified fluid circuit with catchment member.

FIG. 4 illustrates a treatment environment 40 for treating a patient of a disease using the aforementioned ultrasonic therapy systems and methods. The patient 400 is supported on a table, platform, gurney, or other support member 410. In some embodiments the patient 400 is resting on his back substantially as shown, and may be further secured to the support platform 410 with straps or other cushions to limit his movement during treatment and imaging and to provide a safe and comfortable resting place for the patient.

A fluid is circulated into and out of the treatment apparatus as described earlier, and is simplistically represented here as an incoming fluid stream 440 and an outgoing fluid stream 442. The fluid flows through a sterile fluid circuit as discussed earlier and can act to control a temperature at one or more locations proximal to the flowing fluid. Those skilled in the art would appreciate a potential risk from leakage of fluids into the larger imaging and treatment zone. For example, patient body fluids, e.g., urine, may inadvertently be discharged and wet components of the imaging or treatment system. Also, a leak from a fluid coupling or from a rupture in a fluid tubing member can also result in unwanted wetting or shorting of other components in the treatment environment 40. This would be unfortunate in some instances, depending on the amount of fluid leaked, the location of the leak, and the type of components that the leaked fluid comes into contact with. In some cases a risk of electrical shorting or malfunction or interference with the treatment or imaging system could be a concern. Therefore, it is the object of some features hereof to address such fluid leaks if they were to occur.

In one embodiment, a fluid catchment member 420 is provided to catch fluids leaking from or around the treatment region and treatment apparatus. The catchment member 420 may include a waterproof sheet of material 420, which is sized and positioned and formed so as to collect leaking fluid 430 so the leaking fluid does not drain into undesired or harmful locations. The catchment member 420 may be a flexible sheet of disposable spill-proof fabric that can be torn or dispensed from a dispenser, e.g. on a roll, and later discarded as waste. The catchment member 420 may also be formed of a washable plastic or similar material and formed by extrusion for example into a shallow tub that accommodates the patient and other equipment and collects any leaked fluid. Such leak control systems can accommodate a relatively large amount of leaked fluid, and may be able with a suitable drain system as described below to handle an arbitrary amount of leaked fluid.

In yet other embodiments, the catchment member 420 is made of an absorbing material that can hold a substantial amount of fluid (e.g., 50, 250, 500 milliliters or more) if such a fluid 430 were spilled onto the catchment member 420.

Catchment member 420 is optionally provided with a drainage channel 450 which drains collected fluid from the catchment member 420 to a collection container or other non-harmful location. The drainage channel 450 may be in the form of a clear (e.g., Tygon®) tube coupled suitably to a low point of the catchment member 420. A pump or vacuum system may be used to draw spilled fluid 430 from and through the drainage channel 450. The drainage channel 450 may alternatively be formed as a gutter-like channel that is open but still allows for gravity drain movement of leaked fluid 430 away from the treatment zones and sensitive equipment.

In some aspects, it is desirable to have an alarm or warning system to alert technicians or operators to fluid leaks. A moisture sensor, conduction meter, thermometer, fiber optic sensor, or other sensor can be installed at one or more locations in the environment 40 so as to sense if and when a fluid leak has occurred. Upon sensing a leak an alarm or warning signal is sent to a visible or audible alarm siren to alert the operator. The operator can then choose to interrupt the treatment session to investigate it or take other action. A level sensor or float can be placed in a collection reservoir connected to the drainage channel 450 to indicate a minimum accepted leakage in other embodiments. In still other embodiments, pressure sensors in fluid circuit 440-442 or at other locations in the fluid circuit can warn of a loss of pressure in the system, which may indicate a fluid leak or rupture in the system.

The present invention should not be considered limited to the particular embodiments described above. Various modifications, equivalent processes, as well as numerous structures to which the present invention may be applicable, will be readily apparent to those skilled in the art to which the present invention is directed upon review of the present disclosure.

What is claimed is:

1. A fluid control system for use in a thermal therapy system, the fluid control system comprising:
    a treatment chamber including a magnetic shielding wall with a penetration panel;
    a primary fluid circuit located in said treatment chamber and configured to circulate a sterile fluid, said primary fluid circuit including (a) a peristaltic pump that drives said sterile fluid through said primary fluid circuit and (b) an insertable portion of a thermal therapy applicator configured to be insertable into a patient to provide a thermal therapy to said patient;
    a secondary fluid circuit to circulate a secondary fluid, said secondary fluid circuit comprising a first portion located in the treatment chamber and a second portion located outside said treatment chamber, said first and second portions coupled by fluid couplings in said penetration panel, the second portion comprising:
        a chiller configured to receive an output control signal and change a quantity of heat energy in said secondary fluid in response to said output control signal; and
        a second pump that drives said secondary fluid through said secondary fluid circuit;
    a heat exchanger disposed in said treatment chamber, said heat exchanger connected to said primary fluid circuit and said first portion of said secondary fluid circuit such that the sterile fluid is in thermal communication with the secondary fluid;
    a temperature sensor disposed in or on said insertable portion of said thermal therapy applicator to sense a sensed temperature of (a) said sterile fluid or (b) a patient's tissue proximal to a position of said temperature sensor and to provide a corresponding temperature sensor output signal indicative of said sensed temperature; and
    a temperature control circuit configured to receive said temperature sensor output signal, compare said sensed temperature with a set point temperature, and generate said output control signal to control said chiller based on said comparison of said sensed temperature with said set point temperature.

2. The fluid control system of claim 1, wherein the second pump receives a second output control signal from said temperature control circuit to control said driving of said secondary fluid through said secondary fluid circuit.

3. The fluid control system of claim 1, wherein the set point temperature includes a set point temperature range.

4. The fluid control system of claim 1, wherein the second portion of the secondary fluid circuit includes a heater.

5. The fluid control system of claim 4, wherein the temperature control circuit is configured to control the heater using the output control signal.

6. The fluid control system of claim 4, wherein the heater and the second pump are integrated into a single heat pump.

7. The fluid control system of claim 1, wherein the set point temperature is a body's normal internal temperature.

8. The fluid control system of claim 1, further comprising a second temperature sensor disposed between the insertable portion of said thermal therapy applicator and the peristaltic pump.

9. The fluid control system of claim 8, further comprising a first limit switch coupled to said first temperature sensor and a second limit switch coupled to said second temperature sensor, the first limit switch to activate a heating cycle if said sensed temperature is less than a minimum temperature, the second limit switch to activate a cooling cycle if said sensed temperature is greater than a maximum temperature.

10. A method for controlling a fluid in a prostate thermal therapy system, comprising:
    pumping a sterile fluid in a primary fluid circuit, using a first pump comprising non-ferrous components, in a medical imaging and therapy chamber, said primary fluid circuit including an insertable portion of a thermal therapy applicator proximal to which thermal therapy is to be carried out in a patient, said medical imaging and therapy chamber including a magnetic shielding wall;
    measuring a measured temperature of said sterile fluid, using a temperature sensor, and generating a temperature sensing signal corresponding to said measured temperature;
    comparing said temperature sensing signal to a reference signal, said reference signal corresponding to a set point temperature; and
    pumping a secondary fluid, using a second pump, in a secondary fluid circuit that passes through fluid couplings disposed in a penetration panel of said magnetic shielding wall such that said secondary fluid circuit is disposed both inside and outside said chamber, said second pump disposed outside said chamber;
    passing said sterile fluid and said secondary fluid through a heat exchanger disposed in said chamber such that the sterile fluid is in thermal communication with the secondary fluid;
    controlling a chiller to remove heat from said sterile fluid if said measured temperature of said sterile fluid rises above a set point temperature, said chiller disposed outside said chamber.

11. The method of claim 10, further comprising controlling a heater to add heat to said secondary fluid if said measured temperature of said sterile fluid drops below said set point temperature, said heater disposed outside said chamber.

12. The method of claim 10, further comprising controlling the pumping of said secondary fluid based on a difference between the measured temperature and the set point temperature.

13. The method of 10, wherein said temperature sensor is disposed in or on said insertable portion of said thermal therapy applicator.

14. The method of claim 10, further comprising generating an alarm if one or more moisture sensors detects a leak of said primary or secondary fluid circuit.

15. A fluid control system for use in a thermal therapy system, the fluid control system comprising:
- a treatment chamber including a magnetic shielding wall with a penetration panel;
- a primary fluid circuit located in said treatment chamber and configured to circulate a sterile fluid, said primary fluid circuit including (a) a peristaltic pump that drives said sterile fluid through said primary fluid circuit and (b) an insertable portion of a thermal therapy applicator configured to be insertable into a patient to provide a thermal therapy to said patient;
- a secondary fluid circuit to circulate a secondary fluid, said secondary fluid circuit comprising a first portion located in the treatment chamber and a second portion located outside said treatment chamber, said first and second portions coupled by fluid couplings in said penetration panel, the second portion comprising:
  - a heater configured to receive an output control signal and change a quantity of heat energy in said secondary fluid in response to said output control signal; and
  - a second pump that drives said secondary fluid through said secondary fluid circuit;
- a heat exchanger disposed in said treatment chamber, said heat exchanger connected to said primary fluid circuit and said first portion of said secondary fluid circuit such that the sterile fluid is in thermal communication with the secondary fluid;
- a temperature sensor disposed in or on said insertable portion of said thermal therapy applicator to sense a sensed temperature of (a) said sterile fluid or (b) a patient's tissue proximal to a position of said temperature sensor and to provide a corresponding temperature sensor output signal indicative of said sensed temperature; and
- a temperature control circuit configured to receive said temperature sensor output signal, compare said sensed temperature with a set point temperature, and generate said output control signal to control said heater based on said comparison of said sensed temperature with said set point temperature.

16. The fluid control system of claim 15, wherein the second pump receives a second output control signal from said temperature control circuit to control said driving of said secondary fluid through said secondary fluid circuit.

17. The fluid control system of claim 15, wherein the set point temperature includes a set point temperature range.

18. The fluid control system of claim 15, wherein the heater and the second pump are integrated into a single heat pump.

19. The fluid control system of claim 15, wherein the set point temperature is a body's normal internal temperature.

20. The fluid control system of claim 15, further comprising a second temperature sensor disposed between the insertable portion of said thermal therapy applicator and the peristaltic pump.

* * * * *